United States Patent
Fleischlin et al.

(10) Patent No.: US 12,145,002 B2
(45) Date of Patent: Nov. 19, 2024

(54) METHOD AND APPARATUS TO FACILITATE PROPERLY POSITIONING A PATIENT

(71) Applicant: Siemens Healthineers International AG, Steinhausen (CH)

(72) Inventors: Markus Fleischlin, Berikon (CH); Evelyne Waldmeier, Hellikon (CH); Michael Huber, Beinwil am See (CH); Helena Levola, Espoo (FI)

(73) Assignee: Siemens Healthineers International AG, Steinhausen (CH)

(*) Notice: Subject to any disclaimer, the term of this patent is extended or adjusted under 35 U.S.C. 154(b) by 400 days.

(21) Appl. No.: 17/555,808

(22) Filed: Dec. 20, 2021

(65) Prior Publication Data
US 2023/0191155 A1    Jun. 22, 2023

(51) Int. Cl.
*A61N 5/10* (2006.01)

(52) U.S. Cl.
CPC ......... *A61N 5/1038* (2013.01); *A61N 5/1049* (2013.01); *A61N 2005/1059* (2013.01); *A61N 2005/1061* (2013.01)

(58) Field of Classification Search
CPC ............ A61B 1/00147; A61B 1/00172; A61B 1/00194; A61B 1/06; A61B 1/04; A61B 6/04; A61B 6/0492; A61N 5/103; A61N 5/1037; A61N 5/1038; A61N 5/1049; A61N 2005/1041; A61N 5/1047; A61N 5/1031
See application file for complete search history.

(56) References Cited

U.S. PATENT DOCUMENTS

| | | | |
|---|---|---|---|
| 10,166,406 B2 | 1/2019 | Nord | |
| 10,272,265 B2 | 4/2019 | Filiberti | |
| 11,471,702 B2 * | 10/2022 | Meltsner | A61N 5/1031 |
| 2017/0220709 A1 | 8/2017 | Wan | |
| 2017/0281975 A1 | 10/2017 | Filiberti | |
| 2018/0043183 A1 | 2/2018 | Sheng | |

OTHER PUBLICATIONS

Hueso-Gonzalez F. et al.: "An open-source platform for interactive collision prevention in photon and particle beam therapy treatment planning", ARXIV.ORG, Cornell University Library, 201 Olin Library Cornell University Ithaca, NY 14853, Sep. 1, 2021 (Sep. 1, 2021), XP091044277, DOI: 10.1088/2057-1976/ABA442.
International Search Report and Written Opinion from PCT/EP2022/086334; mailed Apr. 13, 2023; 13 pages.

* cited by examiner

*Primary Examiner* — Don K Wong
(74) *Attorney, Agent, or Firm* — Fitch, Even, Tabin & Flannery LLP

(57) ABSTRACT

These teachings provide for accessing stored patient surface information for a given patient and geometry information for a patient support setting. These teachings then provide for generating a patient-position solution that will avoid collisions during a subsequent administration of radiation treatment as a function, at least in part, of that patient service information and the geometry information. That patient-position solution is presented via a user interface in conjunction with conducting at least one simulation scan of the given patient using the patient support setting. To avoid collisions, these teachings will also support an option to modify the treatment plan rather than the patient position using the patient image model shown in the user interface.

18 Claims, 4 Drawing Sheets

METHOD AND APPARATUS TO FACILITATE PROPERLY POSITIONING A PATIENT

TECHNICAL FIELD

These teachings relate generally to treating a patient's planning target volume with energy pursuant to an energy-based treatment plan, and more particularly to properly positioning the patient.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called energy-based treatment plan often serves in the foregoing regards.

An energy-based treatment plan such as a radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters such as individual collimating leaf positions (often while observing one or more corresponding limits in these regards) and mathematically calculating a likely corresponding treatment result to identify a given set of treatment parameters that represent a good compromise between the desired therapeutic result and avoidance of undesired collateral effects.

Unfortunately, existing planning procedures do not necessarily address all potential needs for all potential patients in all potential application settings. Properly positioning the patient represents one such problem area. Poor positioning can become a limiting or even blocking issue during both planning and administration of the treatment. For example, poor positioning during planning can limit the beam arrangement and possible irradiation directions. During delivery of the therapy, poor positioning can lead to situations where parts of the patient are unduly close to the machinery (even to the point of collision).

Generally speaking, patient setup/positioning for such things as computed tomography simulation scanning and/or treatment sessions simply relies on the clinical experience of the technician. That reliance on anecdotal experience and insight can lead to poor patient positioning notwithstanding the best of intentions.

BRIEF DESCRIPTION OF THE DRAWINGS

The above needs are at least partially met through provision of the method and apparatus to facilitate properly positioning a patient described in the following detailed description, particularly when studied in conjunction with the drawings, wherein.

Figure 1:
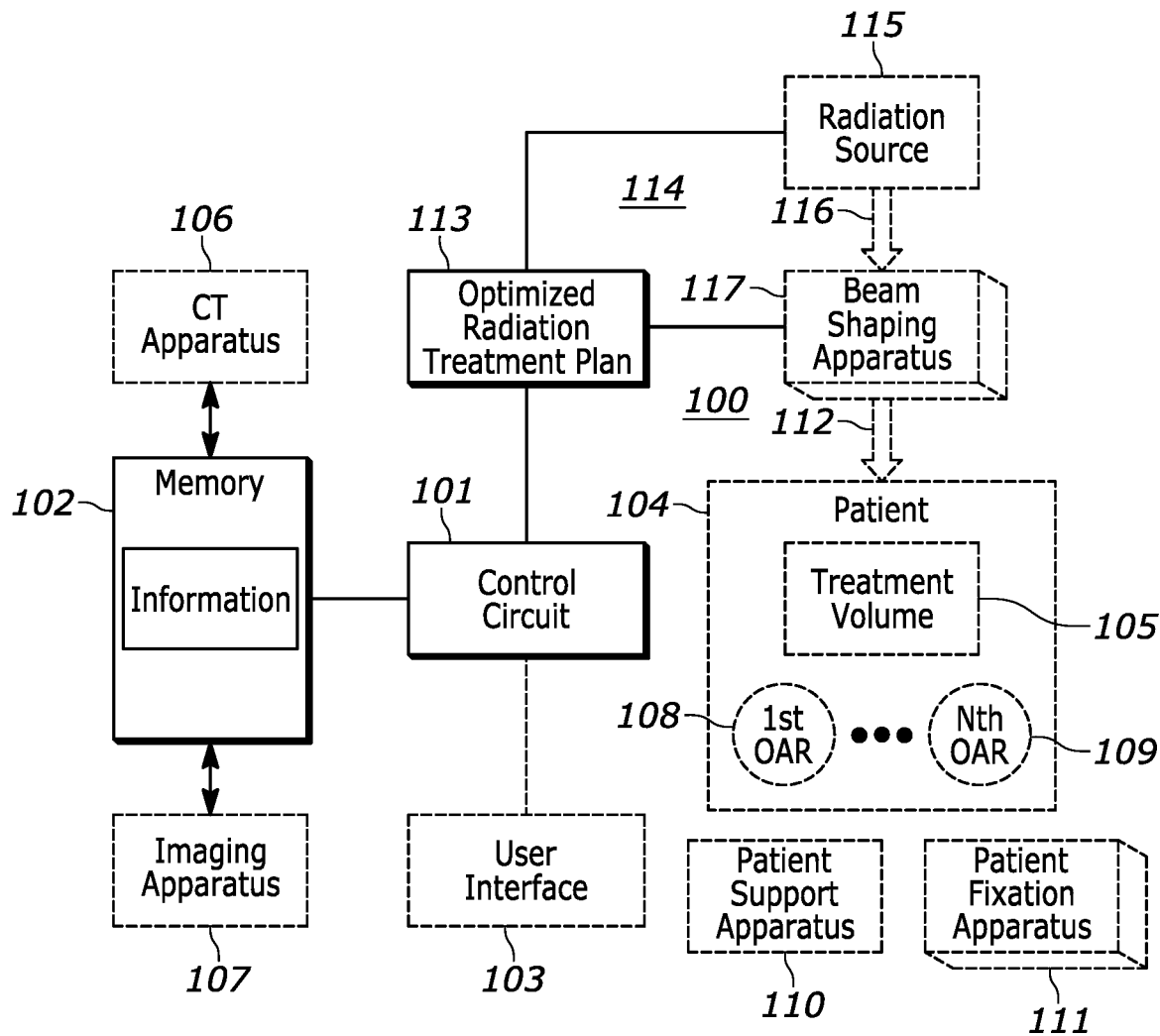
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments serve to facilitate planning a patient radiation treatment plan as well as successfully administering therapeutic energy to a particular patient.

By one approach, these teachings provide for accessing stored patient surface information for a given patient and geometry information for a patient support setting. These teachings then provide for generating a patient-position solution that will avoid collisions during a subsequent administration of radiation treatment as a function, at least in part, of that patient surface information and the geometry information. That patient-position solution is presented via a user interface in conjunction with conducting at least one simulation scan of the given patient using the patient support setting.

By one approach, the aforementioned patient surface information is provided by an optically-based scanner. By one approach, the aforementioned patient surface information includes a three-dimensional model of the given patient. Such a three-dimensional model can be generated, for example, as a function of optical-scanning information generated by an optically-based scanner in combination with computed tomography image information of the given patient.

By one approach, the aforementioned geometry information for a patient support setting can include information regarding patient support surfaces and accessories (e.g. vac bags, braces, etc.), equipment housings, radiation source transport mechanisms, and beam-limiting accessories.

By one approach, these teachings can provide for generating the aforementioned patient-position solution as a function, at least in part, of the aforementioned patient surface information and geometry information in combination with a plurality of radiation treatment plans. By one approach, the radiation treatment plan information can include information regarding corresponding patient surfaces. In lieu of the foregoing, or in combination therewith, the radiation treatment plan information can include information regarding radiation treatment plans for a variety of disease-based circumstances.

By yet another approach, these teachings can provide for generating the aforementioned patient-position solution as a function, at least in part, of the aforementioned patient surface information and geometry information in combination with diagnostic information for the given patient and at least one preferred patient treatment technique.

These teachings will accommodate presenting the patient-position solution in any of a variety of ways. As one example in these regards, the solution can be at least partially presented via a user interface that visually highlights portions of the given patient that need to be adjusted in order to comport with the patient-position solution.

So configured, these teachings provide for defining a patient set up, even at the computed tomography simulation scan stage, that will avoid collisions both during the scan and later during administration of therapeutic radiation via a corresponding radiation treatment plan. More particularly, these teachings do not unduly rely upon the experience of the user and thereby help direct all parties to a useful solution.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as patient surface information for a given patient and geometry information for a patient support setting, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user. Depending upon the needs and/or opportunities presented in a given application setting, this user interface 103 may be positioned to provide information to (and/or receive instructions from) the patient and/or one or more administering technicians.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information. By one approach, the other imaging apparatus 107 can include, for example, an optically-based scanner.

In this illustrative example the control circuit 101 is configured to ultimately output an optimized energy-based treatment plan 113 (such as, for example, an optimized radiation treatment plan). This energy-based treatment plan 113 typically comprises specified values for each of a variety of treatment-platform parameters during each of a plurality of sequential exposure fields. In this case the energy-based treatment plan 113 is generated through an optimization process. Various automated optimization processes specifically configured to generate such an energy-based treatment plan are known in the art. As the present teachings are not overly sensitive to any particular selections in these regards, further elaboration in these regards is not provided here except where particularly relevant to the details of this description.

By one approach the control circuit 101 can operably couple to a radiation treatment platform 114 that is configured to deliver therapeutic radiation 112 to a corresponding patient 104 in accordance with the optimized radiation treatment plan 113. These teachings are generally applicable for use with any of a wide variety of radiation treatment platforms. In a typical application setting the radiation treatment platform 114 will include a radiation source 115 such as a linear particle accelerator-based (linac-based)

x-ray source. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

By one approach this energy source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the energy source 115 along that arcuate pathway, and may accordingly control when the energy source 115 starts moving, stops moving, accelerates, de-accelerates, and/or a velocity at which the energy source 115 travels along the arcuate pathway.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the energy source 115, and one or more energy-shaping apparatuses 117 (for example, beam-shaping apparatuses such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction including rotations around any of those axes) during an energy-based treatment session by the control circuit 101. As the foregoing elements and systems are well understood in the art, further elaboration in these regards is not provided here except where otherwise relevant to the description.

Figure 2:
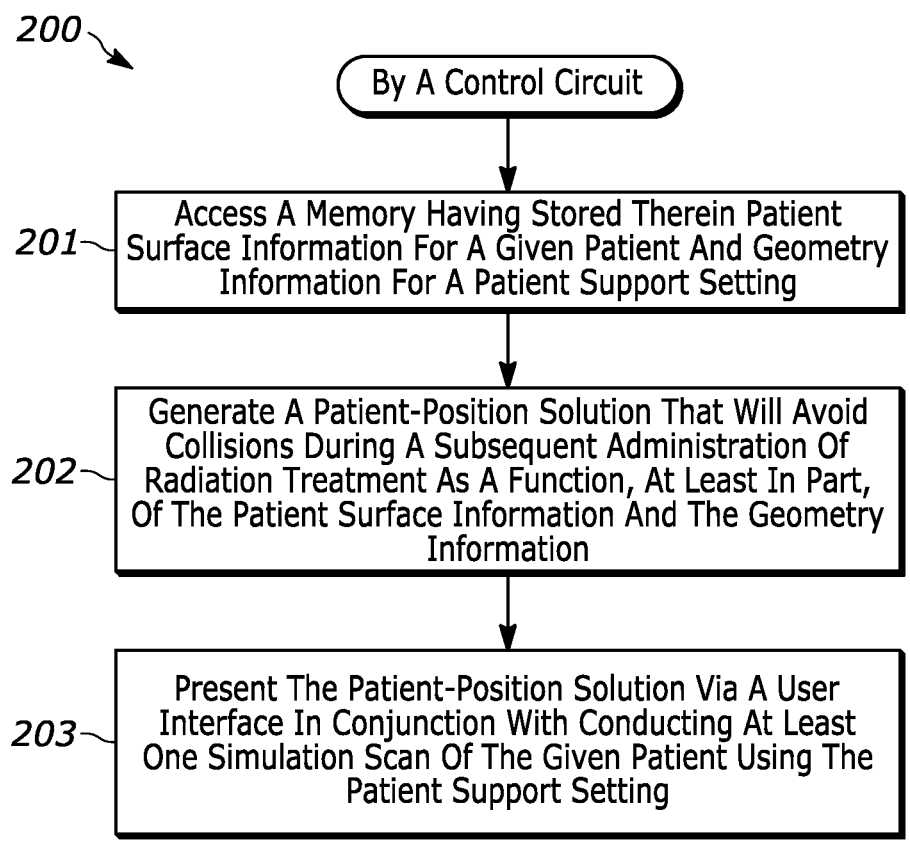
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described.

At block 201, this process 200 provides for the control circuit 101 accessing the aforementioned memory 102 which has stored therein patient surface information for a given patient and geometry information for a patient support setting (as pertains, for example, to the above-described radiation treatment platform 114).

The geometry information can comprise, for example, information regarding the patient support setting in the radiation treatment platform 114. Examples include information regarding patient support surfaces 110, patient fixation apparatus 111, equipment housings, radiation source transport mechanisms, and beam-limiting accessories such as the above-described beam shaping apparatus 117. These teachings will accommodate static geometry information, dynamic geometry information, or both as desired.

The aforementioned patient surface information comprises information detailing the outer surfaces of the patient. By one approach this patient surface information includes optical-scanning information generated by an optically-based scanner that may comprise the above-described imaging apparatus 107. By one approach, this optical-scanning information can be combined with computed tomography image information of the given patient (acquired, for example, via the aforementioned computer tomography apparatus 106) to generate a corresponding three-dimensional model of the given patient. These teachings will accommodate, if desired, optically surface scanning the entirety of the patient during the treatment planning computed tomography session. (It should be noted that such a three-dimensional model of the patient can serve other related purposes. For example, such a model could be used during the radiation treatment planning process to build collision avoidance into the planning process as well.)

At block 202, the control circuit 101 generates a patient-position solution that will avoid collisions during a subsequent administration of radiation treatment as a function, at least in part, of the patient surface information and the geometry information. This patient-position solution comprises a description and/or representation of the patient's general position and/or their pose. A given patient-position solution may be very specific with respect to certain parts of the patient's body but more lax with respect to other parts of the patient's body. For example, the position of one or both arms may be very important but the position of the patient's legs less important.

By one approach, this process 200 can leverage knowledge of other sorts. As one example in these regards, the aforementioned memory 102 may also have stored therein information regarding a plurality of radiation treatment plans. By one approach, that information regarding a plurality of radiation treatment plans may itself include information regarding at least one corresponding patient surface and/or radiation treatment plans for a variety of disease-based circumstances. In such a case, the control circuit 101 may be configured to generate a patient-position solution that will avoid collisions during a subsequent process as a function, at least in part, of the patient surface information, the geometry information, and the plurality of radiation treatment plans. (A "subsequent process" will be understood to refer to the administration of therapeutic radiation, an imaging process, or other process that involves the patient 104 and the radiation treatment platform 114.)

As another example in these regards, the aforementioned memory 102 may also have stored therein information regarding diagnostic information for the given patient and at least one preferred patient treatment technique. In such a case, the control circuit 101 may be configured to generate the patient-position solution that will avoid collisions during a subsequent administration of radiation treatment as a function, at least in part, of the patient surface information, the geometry information, and the diagnostic information and at least one preferred patient treatment technique.

By one approach, this activity may be a single starting point position for the patient (such as lying prone on the patient support apparatus 110 with the patient's arms resting at their sides). By another approach, this activity may include selecting a starting point position for the patient from amongst a plurality of candidate positions. These starting points may, or may not, be correlated with one or more specific planned therapies, diseases, treatment volume locations, and so forth. These teachings will accommodate user selections in these regards and/or partial or fully-automated selection of a starting point position for the patient.

Generation of the patient-position solution can be based, by one approach, upon a simulation of a given patient position within the intended radiation treatment platform 114 during simulation scans and/or therapeutic treatments. Various positions of various body parts can be tested in this way to identify one or more solutions that serve both diagnostic and therapeutic purposes. By one approach, the control circuit 101 can use one or more user-specified metrics regarding required radiation treatment platform surface-to-patient distances that must be observed.

At block 203 of this process 200, the control circuit 101 presents the aforementioned patient-position solution via, for example, the aforementioned user interface 103. More particularly, the solution is presented in conjunction with conducting at least one simulation scan of the given patient using the patient support setting. These teachings will accommodate any of a variety of simulation scans, including computed tomography simulation scans, magnetic resonance imaging-based simulation scans, positron emission tomography-based simulation scans, and so forth. (A simulation scan comprises the acquisition of one or more scan images typically in service of radiation treatment planning. Such a scan is typically used to define tumor and normal organ anatomy by facilitating the segmenting of tumors and organs.)

By one approach, part or all of the solution is presented on one or more display screens. These display screens may comprise a part of the imaging platform or may comprise portable devices used by service technicians or even the patient 104. It will be understood that the solution may be made visible to one or more technicians in the application setting and/or to the patient themselves (the latter to facilitate self-adjustment by the patient to establish a correct position).

Figure 3:
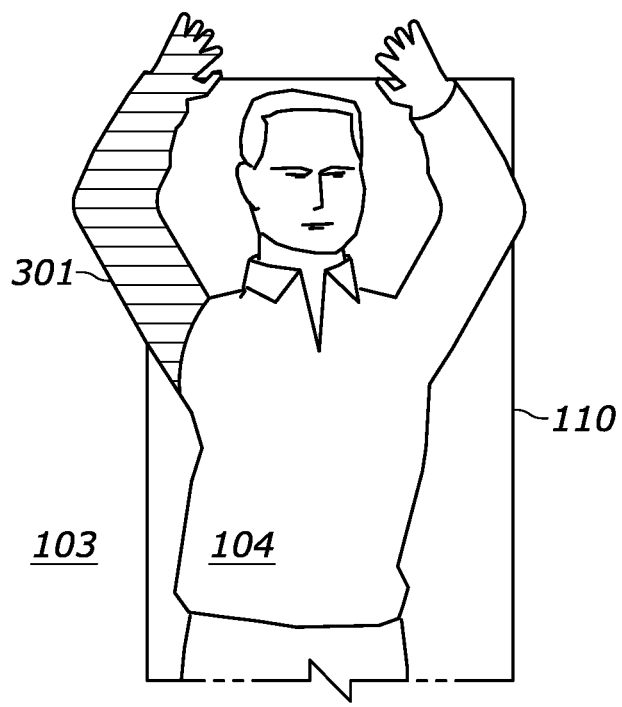
FIG. 3 comprises an illustrative screenshot as configured in accordance with various embodiments of these teachings.
Figure 4:
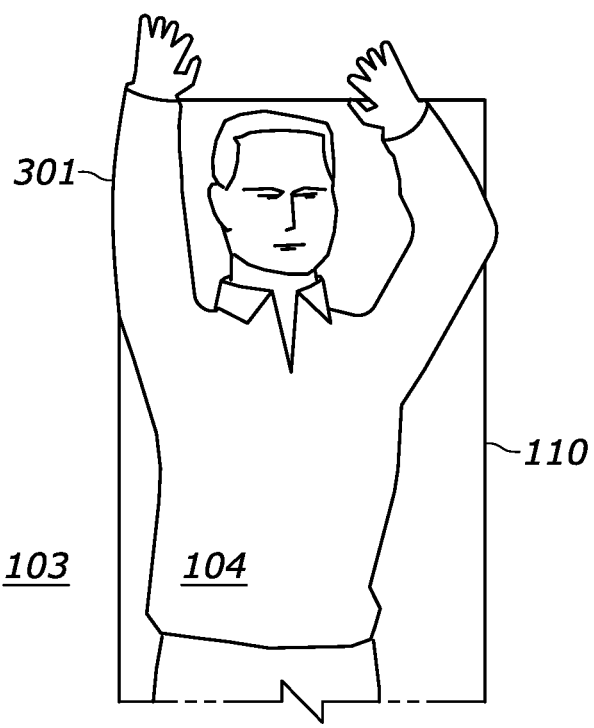
FIG. 4 comprises an illustrative screenshot as configured in accordance with various embodiments of these teachings.

By one approach, presentation of the patient-position solution includes visually highlighting portions of the given patient (or a corresponding avatar) in order to comport with the patient-position solution and/or visually highlighting portions of the given patient that are currently improperly positioned and/or properly positioned. This visual highlighting may be, for example, overlaid on a static or real-time image of the patient or may be a part of a graphic representation of the patient. FIGS. 3 and 4 provide an illustrative example in these regards. In FIG. 3, the patient's right arm 301 is highlighted with a particular distinctive coloration to indicate the incorrect positioning of that arm. Using that information, the patient 104 can move that arm 301 (or an attending technician can move that arm 301) until a correct position is attained. When correctly positioned, and as shown in FIG. 4, the right arm 301 is no longer highlighted as before.

These teachings will accommodate all manner of visually distinctive highlighting approaches. Examples include differing colors, varying translucency/opacity, static or animated arrows, blinking surfaces and/or peripheries, animation (depicting, for example, movement of the body part from a current position to the correct position), and so forth. Audio signals may also be employed if desired. For example, a first audio signal may provide an alert that at least one part of the patient's body is incorrectly positioned, while a second audio signal may confirm that all parts of the patient's body are currently correctly positioned.

If desired, in lieu of the foregoing or in combination therewith, visual highlighting may be projected onto the patient/patient support apparatus to indicate correctly-positioned body parts and/or incorrectly positioned body parts. These teachings will also accommodate providing the patient-position solution via a three-dimensional hologram projection of the current and/or correct patient position.

Figure 5:
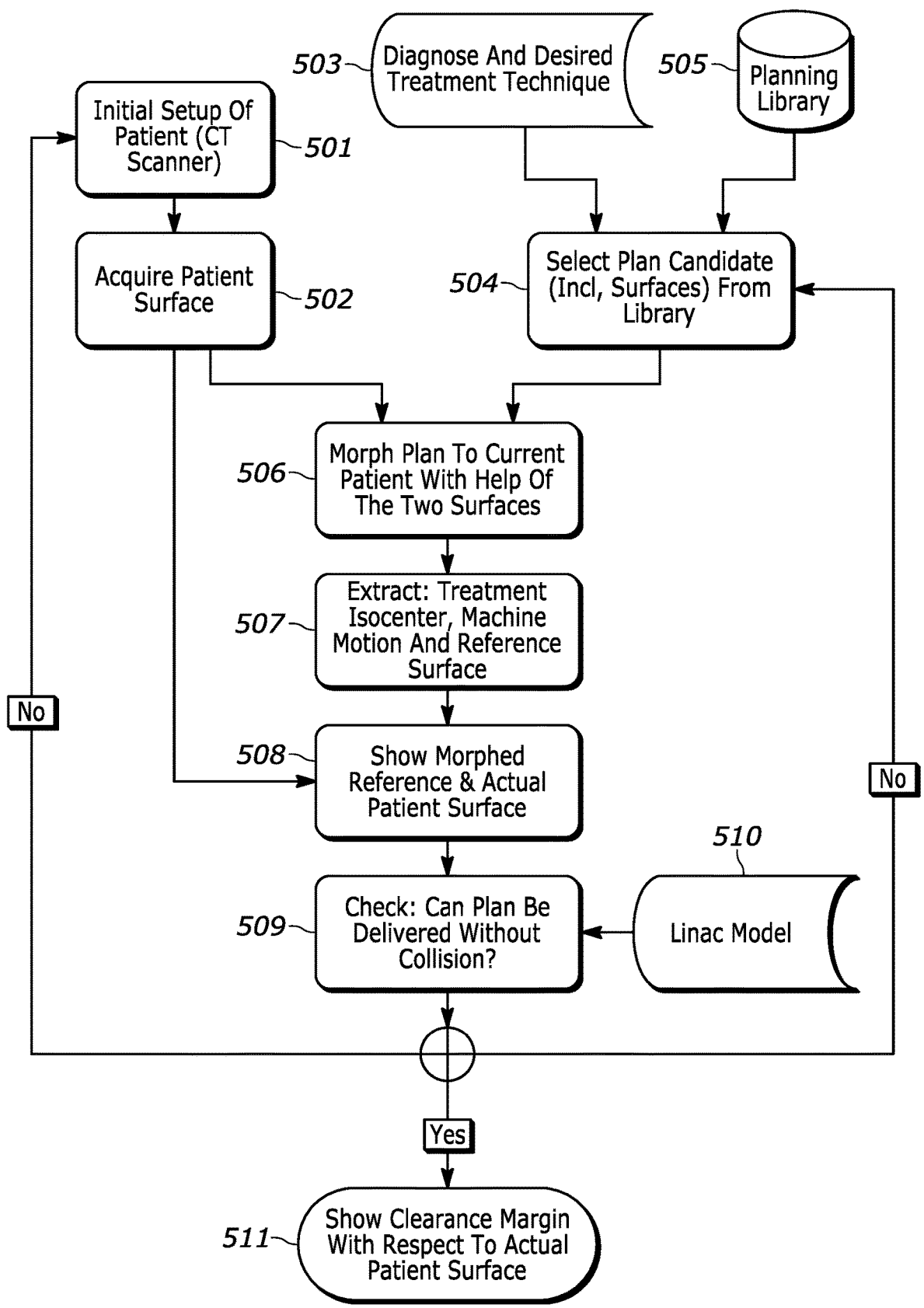
FIG. 5 comprises a flow diagram as configured in accordance with various embodiments of these teachings.

With reference to FIG. 5, a particular approach to generating a reference patient surface will now be described. It will be understood that the details of this description are intended to serve an illustrative purpose and should not be taken as any expression of any limitations regarding the practice of these teachings.

At block 501, this process undertakes initial set up for a given patient using, for example, a computed tomography scanner. At block 502, this process then acquires the patient's surface using, for example, an optically-based scanner. At block 503, this process provides for a corresponding diagnosis of the patient's condition and general selection of a desired treatment technique. At block 504, based upon the foregoing diagnosis and selected treatment technique, this process selects a treatment plan candidate (including corresponding information regarding patient surfaces) from a planning library 505.

At block 506, this process morphs the selected plan to accommodate the particulars of the current patient based upon the computed tomography and optical patient-surface scanning information. At block 507, this process extracts the treatment iso-center, machine motion information, and reference surface information. At block 508, this process will accommodate presenting the morphed reference in contrast to the current actual patient surface.

At block 509, this process provides for determining whether the selected plan can in fact be properly administered without a collision between the treatment setting and the patient. This determination can be based, in part, upon one or more models representing the treatment setting, such as, for example, a TrueBeam c-arm linac. If this determination yields a negative result, the foregoing process can be repeated using fresh information for the patient (reflecting, for example, a new patient pose) and/or an alternative selected plan. If this determination yields a positive result, at block 511 this process can, for example, present information regarding an achieved and/or observed clearance margin(s) between the actual patient surface and one or more features of the application setting.

So configured, these teachings can help facilitate successful radiation treatment plan development and administration that avoids patient-equipment collisions at various stages of such proceedings.

Those skilled in the art will recognize that a wide variety of modifications, alterations, and combinations can be made with respect to the above-described embodiments without departing from the scope of the invention. Accordingly, such modifications, alterations, and combinations are to be viewed as being within the ambit of the inventive concept.

What is claimed is:

1. An apparatus comprising:
  a memory having stored therein patient surface information for a given patient that includes information generated by an optically-based scanner and geometry information for a patient support setting;
  a user interface;
  a control circuit operably coupled to the memory and to the user interface and configured to:
    access the patient surface information and the geometry information;
    generate a patient-position solution that will avoid collisions during a subsequent administration of radiation treatment as a function, at least in part, of the patient surface information and the geometry information;
    present the patient-position solution via the user interface in conjunction with conducting at least one simulation scan of the given patient using the patient support setting.

2. The apparatus of claim 1 wherein the patient surface information includes a three-dimensional model of the given patient.

3. The apparatus of claim 2 wherein the three-dimensional model of the given patient is generated as a function of optical-scanning information generated by the optically-based scanner in combination with computed tomography image information of the given patient.

4. The apparatus of claim 1 wherein the memory also has stored therein information regarding a plurality of radiation treatment plans and wherein the control circuit is further configured to generate the patient-position solution by generating a patient-position solution that will avoid collisions during a subsequent process as a function, at least in part, of the patient surface information, the geometry information, and the plurality of radiation treatment plans.

5. The apparatus of claim 4 wherein the information regarding a plurality of radiation treatment plans includes information regarding at least one corresponding patient surface.

6. The apparatus of claim 5 wherein the information regarding a plurality of radiation treatment plans includes information regarding radiation treatment plans for a variety of disease-based circumstances.

7. The apparatus of claim 1 wherein the geometry information for a patient support setting includes information regarding patient support surfaces, equipment housings, radiation source transport mechanisms, and beam-limiting accessories.

8. The apparatus of claim 1 wherein the memory also has stored therein information regarding diagnostic information for the given patient and at least one preferred patient treatment technique and wherein the control circuit is further configured to generate the patient-position solution by generating a patient-position solution that will avoid collisions during a subsequent administration of radiation treatment as a function, at least in part, of the patient surface information, the geometry information, the diagnostic information, and the at least one preferred patient treatment technique.

9. The apparatus of claim 1 wherein the control circuit is configured to present the patient-position solution via the user interface by visually highlighting portions of the given patient that need to be adjusted in order to comport with the patient-position solution.

10. A method comprising:
by a control circuit:
accessing a memory having stored therein patient surface information for a given patient that includes information generated by an optically-based scanner and geometry information for a patient support setting;
generating a patient-position solution that will avoid collisions during a subsequent administration of radiation treatment as a function, at least in part, of the patient surface information and the geometry information;
presenting the patient-position solution via a user interface in conjunction with conducting at least one simulation scan of the given patient using the patient support setting.

11. The method of claim 10 wherein the patient surface information includes a three-dimensional model of the given patient.

12. The method of claim 11 wherein the three-dimensional model of the given patient is generated as a function of optical-scanning information generated by the optically-based scanner in combination with computed tomography image information of the given patient.

13. The method of claim 10 wherein the memory also has stored therein information regarding a plurality of radiation treatment plans and wherein generating the patient-position solution comprises generating a patient-position solution that will avoid collisions during a subsequent process as a function, at least in part, of the patient surface information, the geometry information, and the plurality of radiation treatment plans.

14. The method of claim 13 wherein the information regarding a plurality of radiation treatment plans includes information regarding corresponding patient surfaces.

15. The method of claim 14 wherein the information regarding a plurality of radiation treatment plans includes information regarding radiation treatment plans for a variety of disease-based circumstances.

16. The method of claim 10 wherein the geometry information for a patient support setting includes information regarding patient support surfaces, equipment housings, radiation source transport mechanisms, and beam-limiting accessories.

17. The method of claim 10 wherein the memory also has stored therein information regarding diagnostic information for the given patient and at least one preferred patient treatment technique and wherein generating the patient-position solution comprises generating a patient-position solution that will avoid collisions during a subsequent administration of radiation treatment as a function, at least in part, of the patient surface information, the geometry information, the diagnostic information, and the at least one preferred patient treatment technique.

18. The method of claim 10 wherein presenting the patient-position solution comprises visually highlighting portions of the given patient that need to be adjusted in order to comport with the patient-position solution.

* * * * *